United States Patent [19]

Krasinski et al.

[11] Patent Number: 5,559,341
[45] Date of Patent: Sep. 24, 1996

[54] SYSTEM FOR DETECTING DEFECTS IN ARTICLES USING A SCANNING WIDTH WHICH IS LESS THAN WIDTH OF PORTION OF THE ARTICLE SCANNED

[75] Inventors: Jerzy S. Krasinski; Yin M. Wang, both of Stillwater, Okla.

[73] Assignee: Minnesota Mining and Manufacturing Company, St. Paul, Minn.

[21] Appl. No.: 381,023

[22] Filed: Jan. 31, 1995

Related U.S. Application Data

[63] Continuation of Ser. No. 117,249, Sep. 3, 1993, abandoned.
[51] Int. Cl.$^6$ .......................... G01N 21/00; G01N 21/86
[52] U.S. Cl. .................. 250/559.26; 250/208.6; 250/559.45; 250/559.48; 356/431; 356/239
[58] Field of Search ................ 250/208.6, 562, 250/572, 563, 559.26, 559.45, 559.48, 559.49; 356/237, 430, 431, 340, 343, 239

[56] References Cited

U.S. PATENT DOCUMENTS

| | | | |
|---|---|---|---|
| 3,202,043 | 8/1965 | Galey et al. | 250/572 |
| 3,361,025 | 1/1968 | Gaffard . | |
| 3,652,863 | 3/1972 | Gaskell et al. | 250/563 |
| 3,737,665 | 6/1973 | Nagae . | |
| 3,748,047 | 7/1973 | Millgard et al. | 356/200 |
| 3,792,930 | 2/1974 | Obenreder | 356/239 |
| 3,814,946 | 6/1974 | Takahashi et al. | 250/572 |
| 3,841,761 | 10/1974 | Selgin | 250/572 |
| 3,984,189 | 10/1976 | Seki et al. | 250/563 |
| 3,992,111 | 11/1976 | Roulier et al. | 356/431 |
| 4,302,108 | 11/1981 | Timson | 356/359 |
| 4,306,808 | 12/1981 | Vander Neut | 356/239 |
| 4,634,281 | 1/1987 | Eikmeyer | 356/239 |
| 4,653,109 | 3/1987 | Lemelson et al. | 382/34 |
| 4,674,875 | 6/1987 | Koizumi | 250/572 |
| 4,775,238 | 10/1988 | Weber | 356/431 |
| 4,882,478 | 11/1989 | Hayashi et al. | 250/208.6 |
| 4,904,877 | 2/1990 | Pietzsch | 250/572 |
| 5,032,734 | 7/1991 | Orazio, Jr. et al. | 250/562 |
| 5,157,266 | 10/1992 | Schmiedl | 250/572 |

FOREIGN PATENT DOCUMENTS

| | | |
|---|---|---|
| 0323564 | 11/1988 | European Pat. Off. ....... G01N 21/89 |
| 880135 | 10/1961 | United Kingdom . |
| 2173294 | 10/1986 | United Kingdom . |

OTHER PUBLICATIONS

International Patent Application No. WO PCT/US91/01421 filed 1 Mar. 1991 Applicant: INTEC CORP.

Primary Examiner—Stephone Allen
Attorney, Agent, or Firm—Gary L. Griswold; Walter N. Kirn; William K. Weimer

[57] ABSTRACT

An apparatus for sensing the deflection of a beam directed at an article detects slight deflection of the beam when the beam is directed at a large angle of incidence. The large angle of incidence increases the apparatus sensitivity to detect certain characteristics within an article which cause slight deflection, and allows the use of smaller optical elements. The apparatus can detect defects such as coating voids, streaks, and caliper variations when transparent materials are coated onto transparent substrates.

53 Claims, 6 Drawing Sheets

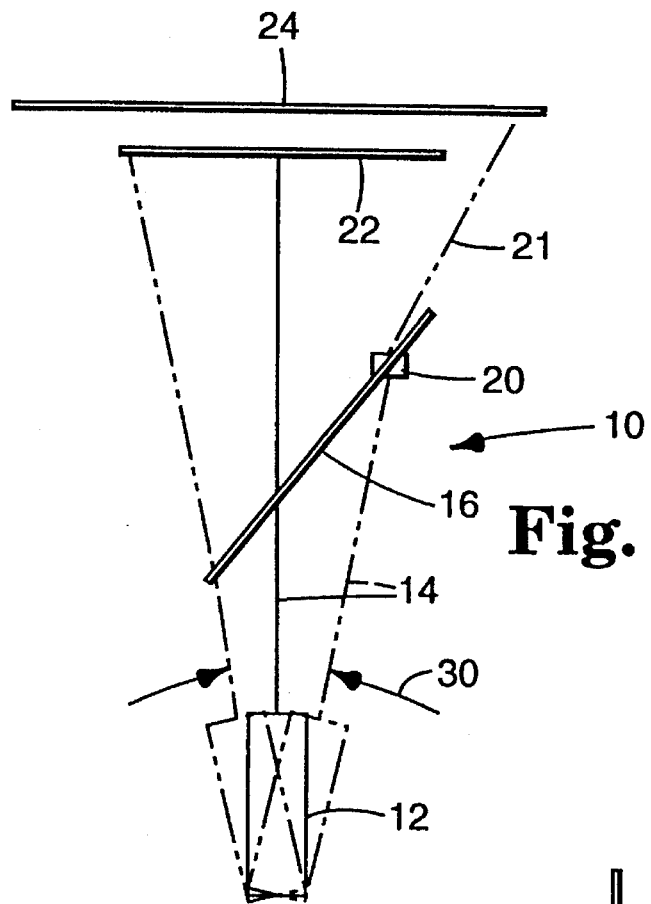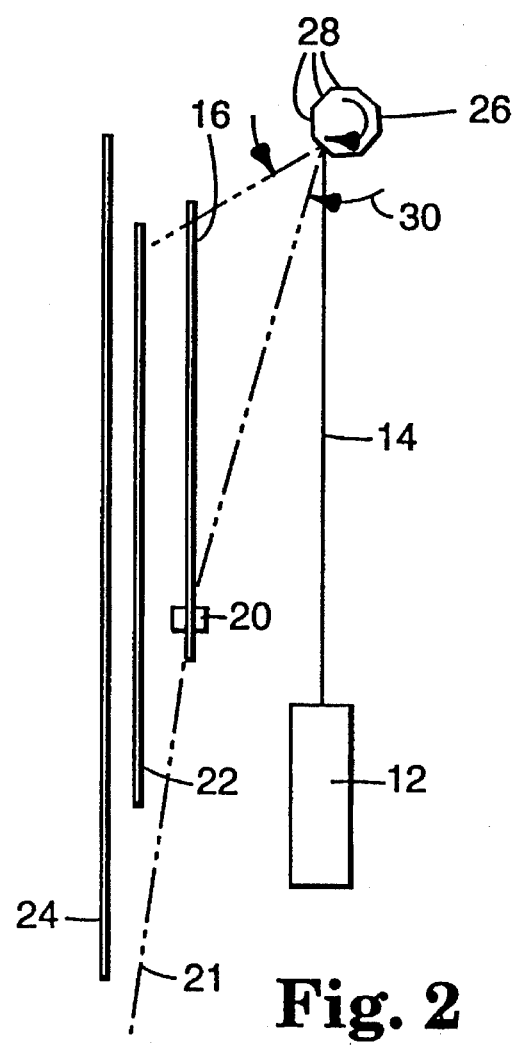

SYSTEM FOR DETECTING DEFECTS IN ARTICLES USING A SCANNING WIDTH WHICH IS LESS THAN WIDTH OF PORTION OF THE ARTICLE SCANNED

This is a continuation of application Ser. No. 08/117,249 filed Sep. 3, 1993, now abandoned.

TECHNICAL FIELD

This invention relates to systems for detecting the deflection of a beam when the beam is directed at an article. More particularly, this invention relates to systems for detecting defects in moving articles, such as webs or films, by detecting the deflection of a beam directed at the article.

BACKGROUND OF THE INVENTION

Detection of defects during production of articles, such as coated films or webs, allows the operator to take prompt corrective action to maximize quality. Fast corrective action is particularly important in the production of continuous articles. Removal or correction of defects in continuous articles can be difficult, and it is often economically prohibitive to separate sections with defects from the defect-free sections of that article. Defects in the center of a wound web or film may require a laborious secondary process to remove the defective sections and to splice the non-defective sections back together. If the web or film is later converted into discrete products, high converting waste can result. In either case, removal of defective sections is often not cost-effective and can result in the waste and disposal of the entire wound web or film.

Effective detection of defects can allow the operator to quickly mark the defects for the secondary removal process. Also, the operator can quickly adjust the primary process in which the defect originates to eliminate the cause of the defect and to minimize defects to an acceptable number. Additionally, detection of "pre-defect" symptoms can prompt the operator to adjust the process to avoid defects prior to their formation. The operator taking the corrective action can be human or automatic.

Apparatus to detect defects are well known. One type of defect-detecting apparatus is an image analyzer which compares an image of the article being inspected with either another image of the article or a programmed image. When the images contrast, the apparatus may consider the irregularity a defect. This type of apparatus can be very expensive depending on the sensitivity required and the type of defects being detected.

Another type of defect-detecting apparatus is the line scanning system. This system includes a laser beam, for example, which is repeatedly directed across the article being inspected. One embodiment of this system includes a photodetector which measures the intensity level of the beam after the beam passes through the article. When the beam is deflected by the article, its intensity is reduced and detected by the system. However, determining changes in intensity resulting from slight deflections is often difficult.

Another known embodiment of this system, rather than measuring intensity levels, includes a scanning beam, which is directed at the surface of the article at a small or zero-degree angle of incidence, and a photodetector having a limited collecting area. A small angle of incidence means that the beam is directed nearly perpendicular to the surface of the article. Directing the beam at a small angle of incidence is used when the beam reflected from the surfaces is also being collected in order to direct the reflected beam away from the source and toward the photodetector. Minimizing this angle is important so that the inspection system takes up the least amount of space.

With this embodiment, when the laser beam travels through the article without being deflected by a defect, the laser beam is collected by the photodetector. If the beam strikes a defect which deflects the beam outside of the collecting area of the photodetector, the failure to collect the beam is sensed by the photodetector.

However, when the beam is deflected by a defect such that the beam still strikes the photodetector, the defect will not be sensed by this system. For example, the deflection due to a defect may be so slight that the beam still strikes a portion of the photodetector. Likewise, if a beam, which when not deflected by a defect strikes one edge of the photodetector, but, in fact, is deflected to just within the other edge of the photodetector, the system will not sense that defect.

It is also known that this type of laser scanning system could be arranged differently so that, rather than collecting an undeflected beam, the undeflected beam is stopped by a masking component. With this arrangement, the photodetector is positioned to collect the beam if the beam strikes a defect which deflects the beam outside of the area of the masking component and within the area of the photodetector. Again, the beam can be deflected by a defect and still be stopped by the masking component causing the system to fail to detect the defect. Consequently, this type of scanning system has a limited sensitivity to defects or variations which cause only slight beam deflection.

In addition, a system of this type which directs a laser across the entire surface of the article and generally perpendicular to that surface uses large optical elements, such as mirrors, lenses, or collectors. The cost of the optical elements required to scan a wide web in this way is significant, and cost-prohibitive for many applications.

Also known is a masking component made up of multiple perforated layers, called a Moire Deflectometer. The perforations of each layer are aligned with the perforations of the other layers such that a beam deflected to a different location within the area of the mask can pass through and strike the photodetector. However, the alignment requires a high degree of accuracy to function and is susceptible to even slight vibration of the article being inspected.

There is a need for a cost-effective scanning system for detecting certain defects in wide articles which cause small deflections of a scanning beam.

SUMMARY OF THE INVENTION

The invention is an apparatus for detecting the refractive deflection of a line scanning beam when the beam is directed at an article at a large angle of incidence. A large incidence angle increases the apparatus sensitivity to detect defects or variations on the surface or within the article which deflect the scanning beam, because the deflection is increased and more easily sensed by the apparatus. This is a significant improvement over apparatus in which the scanning beam is directed at and strikes the defect in the article at a small or zero-degree angle of incidence which can result in only a slight deflection. Furthermore, smaller and less costly optical elements can be used due to the sharp angle of incidence.

The apparatus includes a plate for stopping the scanning beam when the beam passes through the article without being deflected. When the scanning beam is deflected sufficiently off course such that the beam is not stopped by the plate, the beam can, instead, be collected by a collector. Depending on its collection area, the collector will collect the beam deflected within a particular angular range. When the beam is collected, the apparatus has, in effect, sensed a defect which has caused the beam deflection within a certain angular range.

A photodetector can be used to collect the beam, if a laser beam is chosen as the scanning beam. If an electron beam is used, an electron counter can be used in place of the photodetector. Either component collects the beam when the beam strikes the defect and is deflected sufficiently off course by the defect such that the beam is not stopped by the plate.

The apparatus can be used to detect defects in webs. The scanning beam is directed across a portion of the web as the web is transported.

The scanning beam can be focused by a lens or a mirror. A rotating, multi-sided scanner can receive the focused beam and direct it across an angular range. A first concave mirror can convert the angular range of the beam to a parallel range. This first concave mirror can also focus the beam across the moving web at a large angle of incidence with the web. A second concave mirror can converge the parallel range of the beam to an angular range after the beam leaves the web unless the beam has been sufficiently deflected to avoid striking the second mirror.

BRIEF DESCRIPTION OF THE DRAWINGS

FIG. 1 is a schematic view of an apparatus according to the present invention for sensing the deflection of a beam when the beam is directed at an article at a large angle of incidence.

FIG. 2 is a schematic view of another embodiment of an apparatus including a multi-sided reflector.

DETAILED DESCRIPTION OF PREFERRED EMBODIMENTS

Figure 3A:
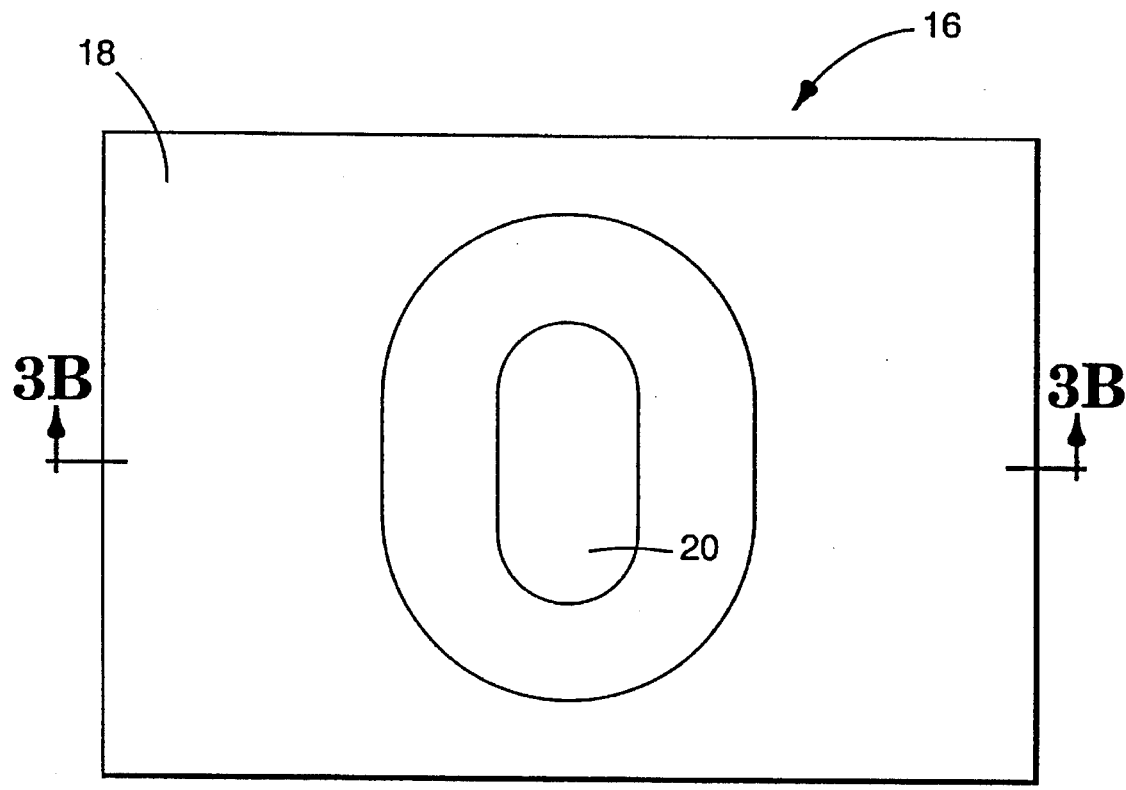
FIG. 3A is a top view of an elliptically-shaped, coating void defect on an article.

This invention is an apparatus for detecting defects or variations in articles by detecting the deflection of a line scanning beam off an article when the beam is directed at the article. The apparatus can detect refractive deflection of the beam when the beam is directed at a transparent article at large angles of incidence, defined as 30–90 degrees. The large angle of incidence increases the apparatus sensitivity to detect certain characteristics within an article which cause slight refraction of the beam. In addition, the large angle of incidence reduces the size of the optical elements required to scan wide articles. The term "article" designates all types of materials which can be inspected by using the present invention, including sheets, films, and webs, whether or not these materials are coated. The term "transparent" means that the article being inspected is permeable to the scanning beam. The transparency of an article can depend on the composition of the article and the wavelength of the scanning beam. For example, plain window glass is transparent to a visible light scanning beam. In addition to glass, the invention is effective to detect defects in other transparent materials such as polymeric sheets and films, including acrylics, polycarbonates, polyesters, polypropylenes, and polyethylenes. In addition to these materials, the present invention can be used with woven or non-woven webs, such as spunbonded or carded webs.

The term "defect" means the presence of an attribute in or on the article which the apparatus is designed to detect. This definition includes unwanted variations, as well variations which are desired, such as surface roughness. Common defects in films, in particular, include caliper variations and gels. When transparent coating materials such as adhesives and primers are coated onto transparent substrates, defects include coating voids, streaks, and caliper variations. A coating applied in the form of a solution often must be dried to evaporate off the solvent which can result in a very thin dry coating. A void in a thin coating, resulting when the coating caliper decreases at a very small angle to the substrate until an area of the substrate is not coated, can be detected by this apparatus.

The goal of the inventors in developing this invention was a system for detecting coating voids on films created on wide production equipment. In developing this invention, the inventors unsuccessfully attempted to detect these voids on transparent films in several ways. First, using a small pilot line, the inventors attempted to measure the intensity of the beam after the beam either passed directly through the coated film or was deflected by a defect. However, the inventors learned that slight changes in the intensity of the beam were not easily measured. Consequently, coating void defects and other defects which caused slight intensity changes were not easily detected.

Then, the inventors attempted to detect the voids by detecting the deflection angle of a laser beam directed at coated film at an angle perpendicular to the surface of the coated film, that is, at approximately a zero-degree angle of incidence. A plate was positioned on the opposite side of the film to stop the beam if it were not deflected. A photodetector was used to collect the beam which was deflected by coating voids and not stopped by a plate. A first concave mirror, equal in size to the width of the test film, was used to direct the beam at the film. A second, equal-sized concave mirror was used to converge the beam onto a plate which stopped the beam if the beam was not deflected by a defect.

The inventors discovered two important features. First, although they were able to detect certain defects, this apparatus was unable to detect coating voids which caused only slight deflection the beam. The slight deflection angle was insufficient to avoid the plate. Second, even if this apparatus were able to detect voids as desired by the inventors, scaling up this apparatus would require at least 60-inch concave mirrors to inspect a 60-inch wide production coating line. Two concave mirrors, or other optical elements, of this size and reasonably high quality were simply not a cost-effective way of detecting coating voids on a single production coating line. Furthermore, the inventors knew that several pairs of optical elements would be required to outfit several production coating lines. After much consideration of these problems, the inventors developed the present system.

As shown in FIG. 1, one embodiment of the apparatus 10 includes a beam source 12 which directs or scans a beam 14, such as a laser beam, across at least a portion of an article 16. A plate 22 stops the beam 14 which has not been sufficiently deflected off course by a defect 20, such as a coating void, streak, or caliper variation, in the article 16. A detector 24, such as a photodetector, located behind the plate 22, collects the deflected beam 21 which is deflected off course and away from the plate 22 by striking the defect 20 in the article 16.

The wavelength of the laser beam is chosen to be compatible with the composition of the article being inspected for the purpose of permitting inspection. Alternatively, an electron beam can be used, and an electron counter (not shown) is used in place of the photodetector 24. Other compatible beam and collector combinations, such as ultrasonics, are possible.

The apparatus 10 can include an alarm (not shown) which would sound when the photodetector 24 collects a deflected beam 21, prompting an operator, for example, to mark the defect 20, or to correct the defect cause, or both. Alternatively, the apparatus 10 can include a microprocessor (not shown) which would instruct another apparatus to mark, locate, or count the defects or to correct the defect cause, or some combination of these tasks.

Although the apparatus 10 is described as stationary and scanning a moving article 16, the apparatus 10 could also scan across a stationary article as the apparatus travels down the length of the article 16. In either case, the defect-detecting sensitivity depends on the speed at which the beam 14 is directed across the article 16, and on the speed of the article 16 relative to the apparatus 10.

The beam 14 of FIG. 1 is directed across the web 16 by pivoting the beam source 12 back and forth over an angular range 30. As shown in FIG. 2, the source 12 can be stationary, with the beam 14 directed across the web by focusing the beam 14 at a scanner, such as a rotating reflector 26 having multiple reflective sides 28. As the reflector 26 rotates, the beam 14 is repeatedly directed over an angular range 30. The angular range 30 depends on the number of reflective, flat sides 28 and on the distance between the scanner 26 and the article 16.

The plate 22 has a surface area and shape which stops the scanning beam 14 unless the beam 14, is sufficiently deflected by a defect or variation in the article 16. The shape of the plate 22 can be, for instance, a circle, oval, rectangle, or square. In FIGS. 1 and 2, the plate 22 is shown stopping the undeflected scanning beam 14.

The photodetector 24 collects the beam when the beam 14 is deflected off course due to the defect 20 and due to the large angle of incidence such that the beam 14 is not stopped by the plate 22, but is within the perimeter of the photodetector 24. The photodetector 24 does not collect the scanning beam 14 if the beam is deflected beyond the perimeter of the photodetector 24. Known inspection systems which use small angles of incidence are unable to detect defects that cause beam deflection insufficient to avoid the plate 22 when the defect is small. Consequently, the angle of incidence must be chosen so that the apparatus 10 can detect the slight deflection due to the decreasing coating caliper near a coating void defect.

The size and shape of the photodetector 24 is a factor in determining what deflection angles the apparatus 10 will detect, and therefore what types of defects will be detected. Like the plate 22, the shape of the photodetector 24 can be, for example, a circle, oval, rectangle, or square. As shown in FIG. 1, the photodetector 24 has collected the beam 21 which was deflected slightly outside of the perimeter of the plate 22.

As shown in FIG. 2, however, the photodetector 24 has not collected the beam 21 which was deflected outside of the perimeter of the photodetector 24. Defects which cause deflections of this magnitude, such as surface scratches, are overlooked in this case. Also, the photodetector 24 will not collect the beam 14 which is insufficiently deflected and still is stopped by the plate 22.

Figure 3B:
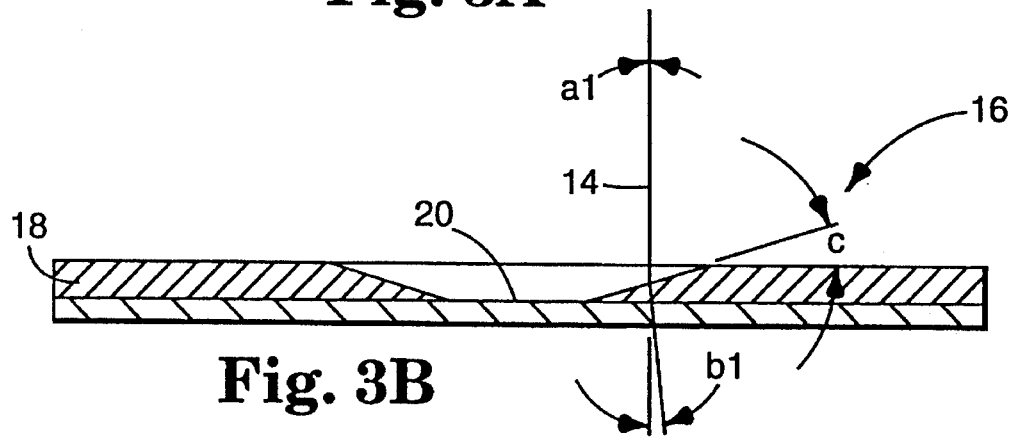
FIG. 3B is a cross-sectional view taken along line 3B—3B of FIG. 3A and showing a beam directed at an angle of incidence perpendicular to the article.

In FIG. 3A, a thin coating 18 on the article 16, shown as a film, has a defect 20 in the form of a coating void. The coating 18 has an index of refraction of approximately 1.4. The angle c of the coating surface leading to the void defect 20 is approximately 0.5 degree. (This angle is exaggerated for illustration.) As shown in FIG. 3B, the beam 14 is directed at a zero-degree or small angle of incidence a1, that is, generally perpendicular to the article 16. The deflection angle b1, which is determined by the incidence angle, the angle at which the caliper of the coating 18 is decreasing near the void defect 20, and by the index of refraction of the coating 18, is approximately 0.2 degree.

Figure 4:
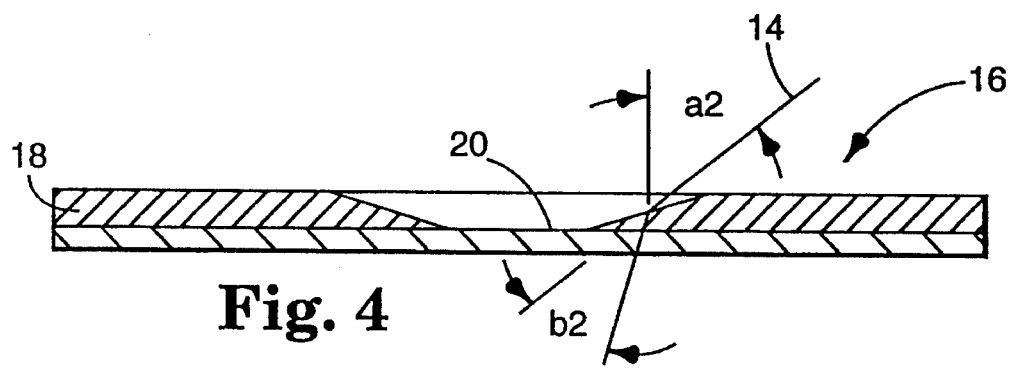
FIG. 4 is a cross-sectional view taken along line 3B—3B of FIG. 3A and showing a beam directed at a large angle of incidence to the article.

In FIG. 4, the scanning beam 14 is directed at the same article 16 at a large angle of incidence a2. Where a2 is approximately 80 degrees, and the same void angle c and index of refraction of the coating 18 are used, the resulting deflection angle b2 is 2.16 degrees (this angle is exaggerated for illustration), which is approximately ten times larger than the refraction angle b1 shown in FIG. 3B. The apparatus of the present invention takes advantage of this increase in inspection sensitivity using a large angle of incidence. In addition, when an 80-degree incidence angle is used, the size of the optical elements, such as the two mirrors 36, 40 shown in FIG. 7, can be approximately one-fifth the size of the mirrors had the beam 14 been directed perpendicular to the article 16, while still inspecting the same size web with all of the other parameters kept the same.

Although directing the beam 14 at the article 16 at an incidence angle a2 larger than 80 degrees increases the deflection angle and allows for smaller optical elements, the inventors found that other problems arise. First, a greater percentage of the beam is reflected off the surface of the article 16 rather than passed through the article 16. Second, the adverse effect of vibration of the article 16 is increased. Vibration of the article changes the angle at which the scanning beam 14 strikes the article 16 which can cause the apparatus to make false readings. For instance, a defect can be missed entirely, or the defect can appear to be located at a position on the article other than where it is actually located. Consequently, the choice of the optimum incidence angle a2 of approximately 80 degrees is a compromise to obtain the necessary sensitivity and allow for smaller, lower cost optical elements while minimizing the two problems mentioned above.

Figures 5, 6:
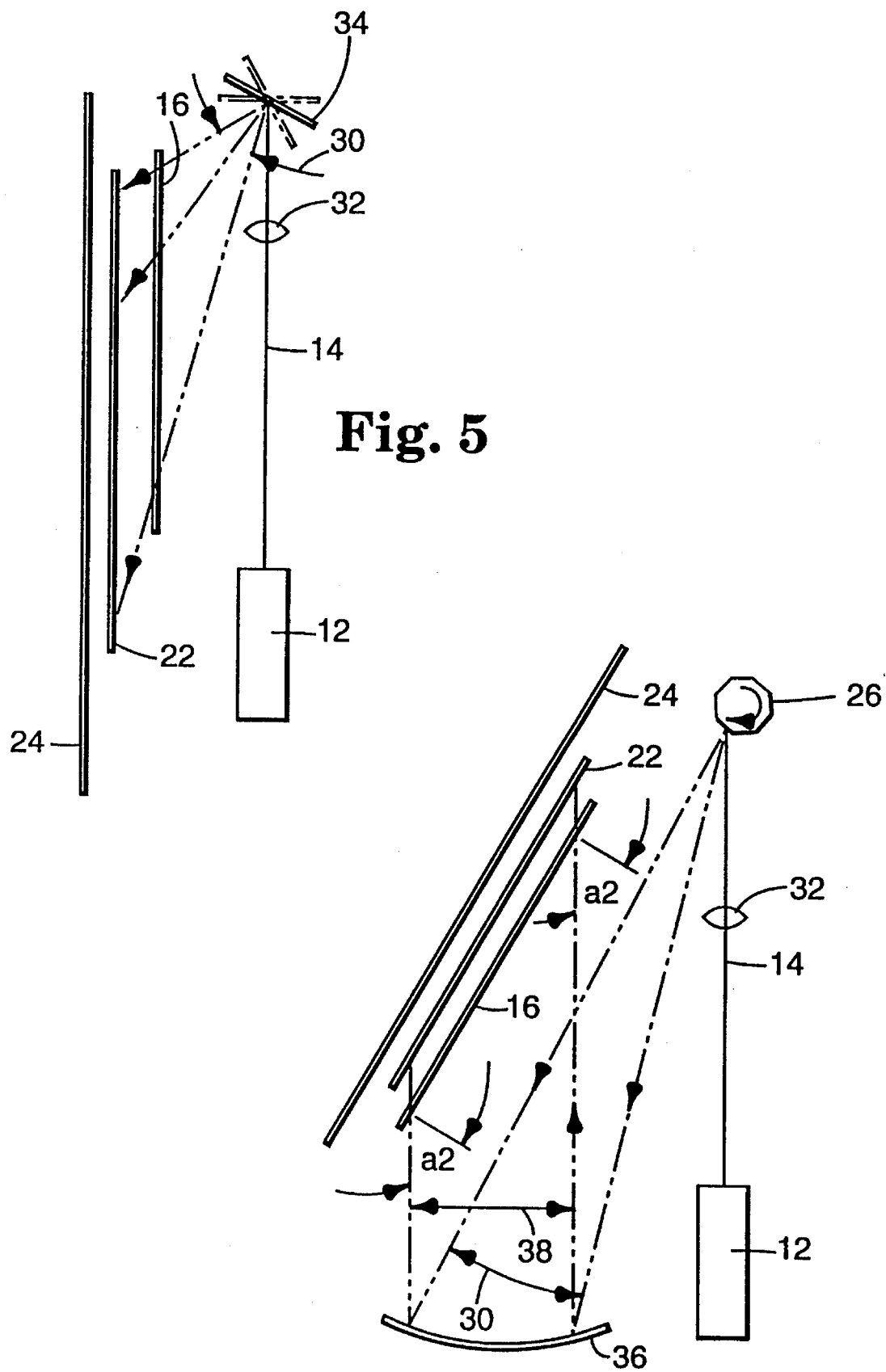
FIGS. 5, 6, 7, 8, 9 and 10 are schematic views of additional embodiments of the apparatus for detecting the deflection of a beam when the beam is directed at an article.

Another way to accomplish the same result as the rotating reflector 26 is to focus the beam 14 at a single reflective surface 34 which pivots back and forth, as shown in FIG. 5. Similarly, a movable lens (not shown) could be used in place of the reflective surface 34.

Also shown in FIG. 5, a lens 32 can be added between the beam source 12 and the scanner to reduce the diameter of the beam 14 to more accurately focus the beam 14 on the article 16. In place of the lens 32, a mirror, an anamorphic prism, or other beam-correcting devices (not shown) could be used.

As shown in FIG. 6, a concave mirror 36 can be added to receive the directed beam 14 and convert its range 30 to a generally parallel range 38 before striking or passing through the article 16. When the beam 14 is directed across the article 16 witch a parallel range 38, the beam 14 strikes the article 16 within the entire range 38 with the same angle of incidence a2. This creates consistency in the deflection angle for similarly sized and shaped defects which allows the apparatus to be adapted to detect defects of only a desired size.

Rather than convert the angular range 30 to a parallel range 38, a mirror having greater concavity (not shown) can be used to converge the diverging range 30. The convergence caused by this mirror, however, can disrupt the consistency of the angle of incidence a2 across the article 16.

Figure 7:
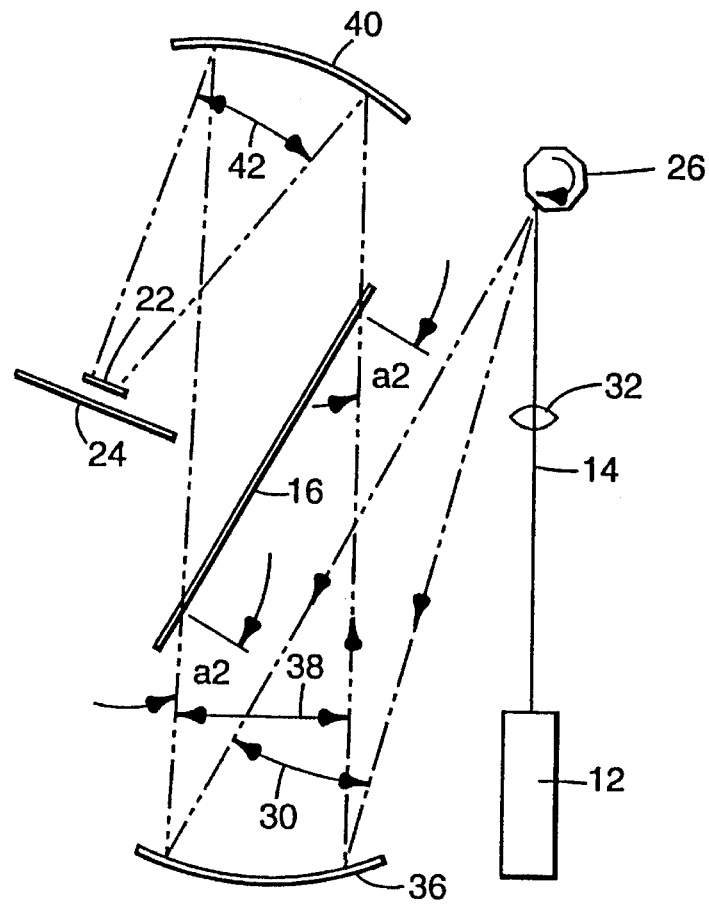

Another embodiment of the invention includes, as shown in FIG. 7, a second concave mirror 40 to receive the generally parallel range 38 of the beam 14 after striking the article 16 and to converge the beam to an angular range 42 on either the plate 22 or the photodetector 24. Converging the parallel range 38 to the angular range 42 after the beam 14 leaves the article 16 allows for the use of a smaller plate 22 and a smaller photodetector 24 without affecting the consistency of the angle of incidence a2. Consequently, converging the range increases the sensitivity of the apparatus to detect defects which cause slight deflection of the beam 14.

Sensitivity of the apparatus of FIG. 6 can be further increased by increasing the distance between the article 16 and the plate 22. As this distance increases, smaller deflection angles will cause the beam to miss the plate and strike the detector. This method has practical limitations with respect to availability of the adequate process area and component sizes. Consequently, it is convenient to converge the beam as presented in FIG. 7 and place a small beam stopping plate 22 at the focal plane, also called a Fourier plane, of the focusing element 40. This arrangement offers high sensitivity.

If the plate 22 is located at the point of convergence of the angular range 42, the area of the plate 22 need only be as large as the cross-sectional area of the beam. Similarly, if the cross-sectional shape of the beam 14 at the point of convergence is circular, the shape of the plate 22 could be round. However, if the plate 22 is located at other than the point of convergence, the plate 22 should be shaped and sized to stop the width of the scanning line (not shown) of the beam 14 which depends on the distance between the plate 22 and the point of convergence of the angular range 42.

Figure 8:
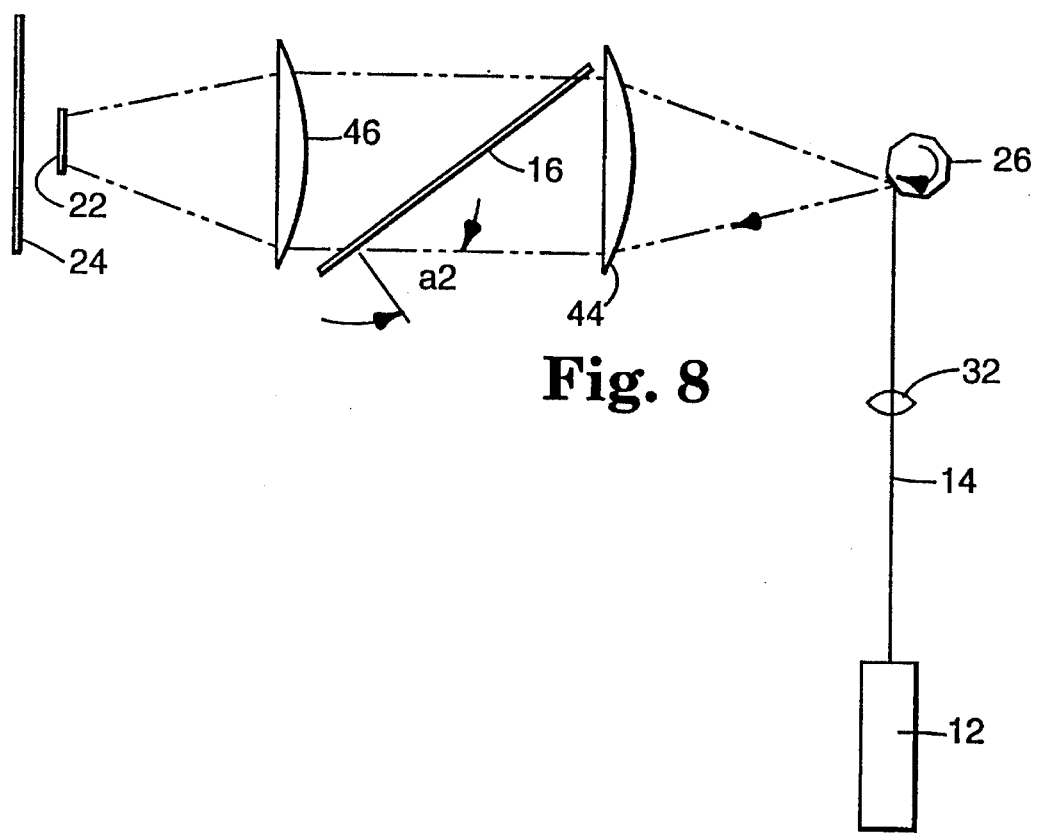

Another embodiment of the apparatus 10 could include lenses 44, 46, as shown in FIG. 8, which would replace the concave mirrors 36, 40 shown in FIG. 7.

Figure 9:
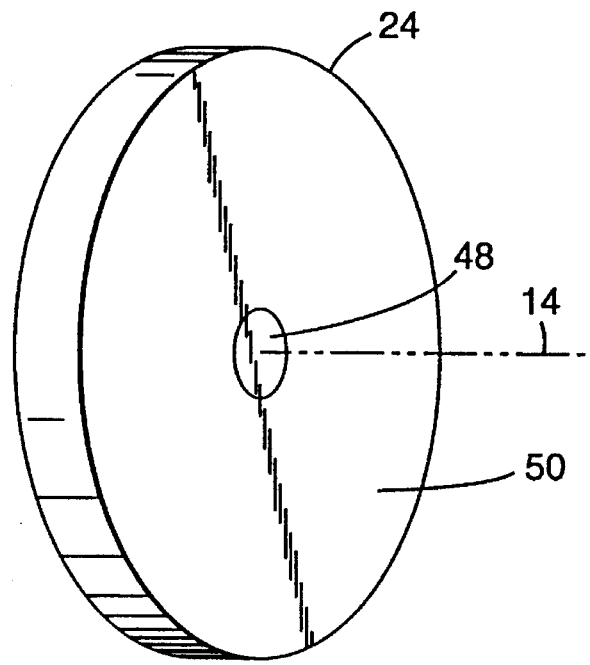

Another embodiment of the apparatus 10 could include an annular photodetector 24 as shown in FIG. 9. The central portion 48 of the photodetector surface, which can have either no photosensitivity or a different degree of photosensitivity than the outer annular portion 50 of the photodetector 24, can be equal to the area of a plate 22. Therefore, no plate is required. When the beam 14 strikes the central portion 48, no defect is detected. Alternatively, the photodetector 50 can be formed without the central portion 48. When the beam 14 is undeflected, it passes through the hole.

Figure 10:
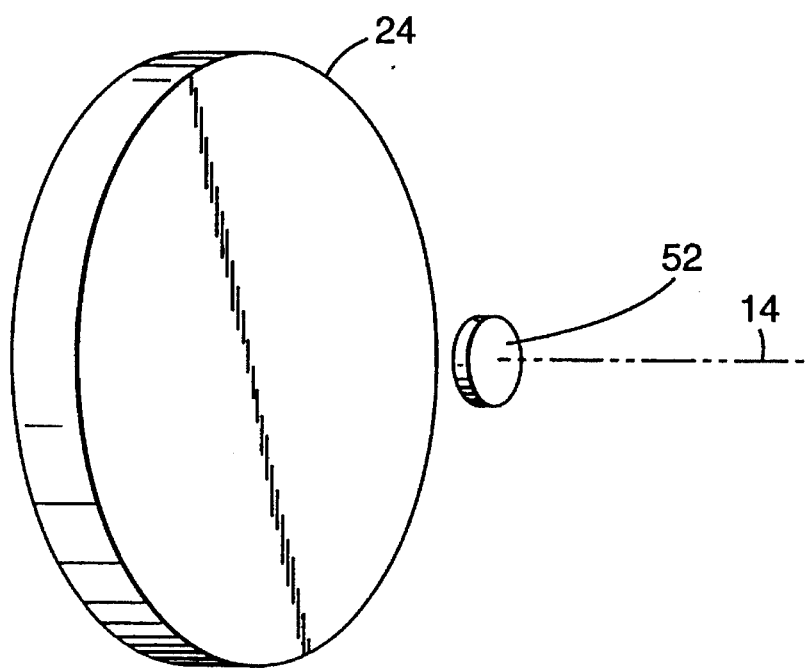

Another embodiment of the apparatus 10 could use an additional photodetector 52 in place of the plate 22 located in front of the existing photodetector 24, as shown in FIG. 10. The front photodetector 52 would collect the undeflected beam 14 and the beam 14 if deflected insufficiently to avoid the front photodetector 52. The rear photodetector 24 has a size which is chosen to collect the beam deflected within a desired deflection range. Deflection beyond the perimeter of the rear photodetector 24 would not be collected.

With this two-photodetector arrangement, the apparatus 10 could detect two groups of defects. In addition to detecting defects which deflect the beam 14 to the rear photodetector 24, the apparatus 10 would detect defects which deflect the beam 14 beyond the perimeter of the rear photodetector 24 by sensing the absence of the beam 14 by both the front photodetector 52 and the rear photodetector 24. Similarly, additional photodetectors could be added behind these two photodetectors and be incrementally larger than the two photodetectors to detect multiple groups of defects which cause incrementally larger deflections.

To gain the same effect as locating larger photodetectors behind a smaller photodetector, numerous rings of increasing larger diameter photodetectors could be joined together along the same collection plane (not shown). The centerpoint of the rings could be located at the focal point of the converging beam range and collect the beam when no deflection occurs. The diameter of each ring could be chosen to collect a range of deflection angles.

Figure 11:
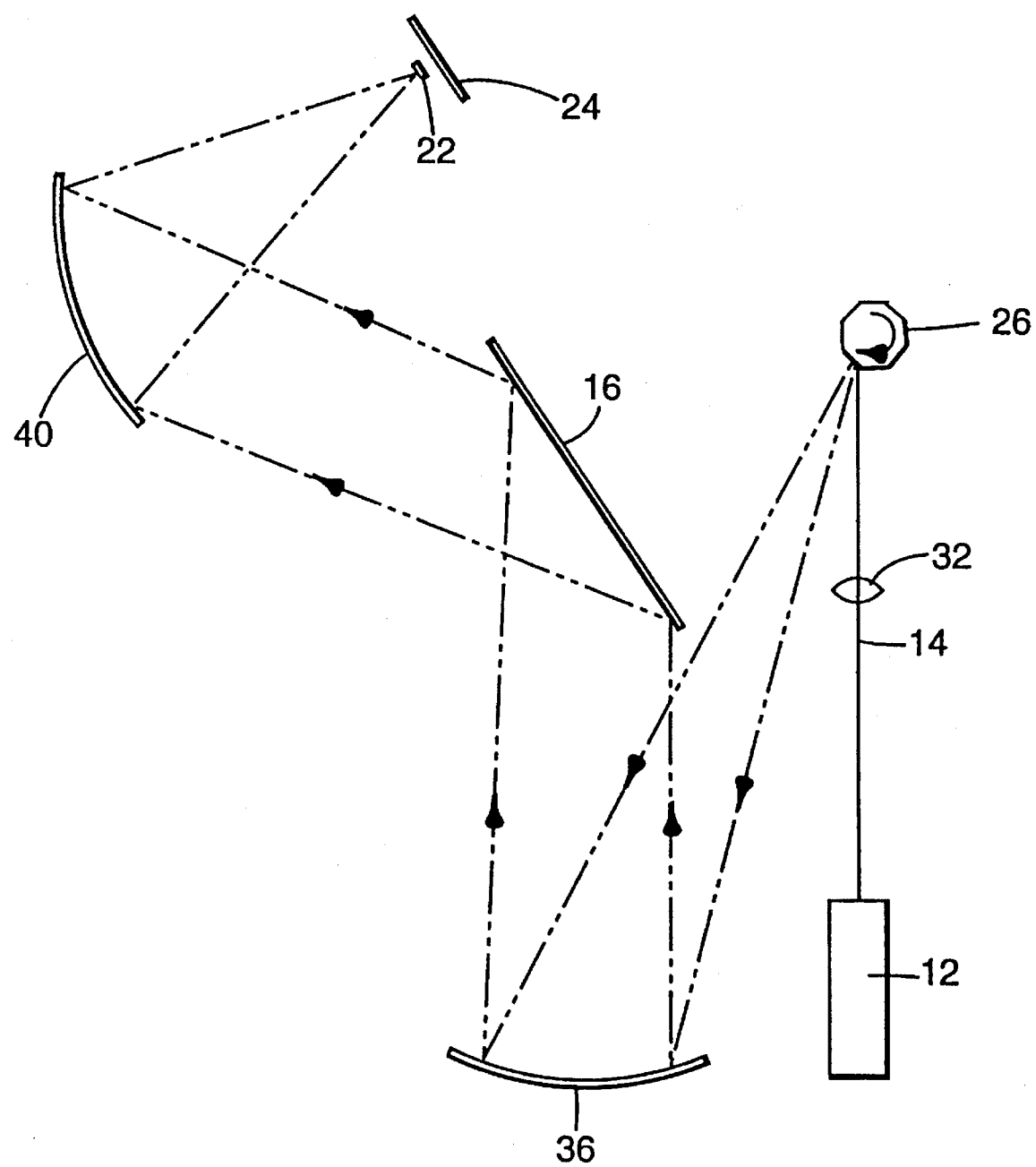
FIG. 11 is a schematic view of another embodiment of the apparatus for detecting the reflective deflection of a beam when the beam is directed at an article.

Another embodiment of the apparatus 10, shown in FIG. 11, could detect slightly deflecting defects or surface variations in metallic or other reflective webs, such as metal foils and retroreflective traffic control materials. The stop plate 22, photodetector 24, and second concave mirror 40 are positioned to receive the beam reflected off the surface of the article 16 being inspected.

All embodiments could include multiple beams, rather than the single beam 14. This would increase defect detection by more closely scanning the article. Additionally, multiple beams striking a defect 20 from different angles can reduce the chances of not detecting a defect which significantly deflects the beam 14, but where the beam is still stopped by the plate 22.

The invention, in addition to an apparatus, includes a method of detecting defects or variations within articles by detecting the deflection of a line scanning beam when the beam is directed at the article at a large angle of incidence. Use of the large angle allows for the use of smaller, less costly optical elements.

We claim:

1. An apparatus for detecting defects in a transparent article which cause the deflection of a scanning beam when the beam is directed through the transparent article, the transparent article having a side edge, the apparatus comprising:

means for directing a scanning beam through the transparent article at an angle of incidence ranging from 70 degrees to 90 degrees and such that the beam approaches the transparent article from beyond the side edge;

means for stopping the beam when the beam passes through the transparent article and is not sufficiently deflected by the defect in the transparent article; and means for collecting the beam when the beam is deflected sufficiently off course by striking the defect as the beam passes through the transparent article such that the beam is not stopped by the stopping means but not deflected beyond the perimeter of the collecting means.

2. The apparatus of claim 1 further comprising a scanning beam which is a laser beam having a wavelength which is selected in combination with the composition of the article being inspected, and wherein the collecting means comprises at least one photodetector.

3. The apparatus of claim 1 further comprising means for moving the article relative to the scanning beam, and wherein the article comprises a coated film.

4. The apparatus of claim 1 wherein the stopping means comprises a plate, and wherein the collecting means sends a signal indicating the presence of a defect.

5. The apparatus of claim 1 wherein the stopping means comprises a photodetector.

6. The apparatus of claim 1, wherein the angle of incidence ranges from 75 degrees to 85 degrees.

7. The apparatus of claim 1, wherein the angle of incidence is approximately 80 degrees.

8. The apparatus of claim 1, the transparent article having a side edge, the directing means comprising means for directing the scanning beam such that the scanning beam approaches the article from beyond the side edge.

9. The apparatus of claim 1 wherein the directing means comprises a scanner which directs the beam across a desired angular scanning range.

10. The apparatus of claim 9 wherein the directing means further comprises means for creating consistency of the angle of the beam across the entire article by focusing the angular scanning range of the beam created by the scanner into a generally parallel scanning range before the beam has either struck a defect or passed through or reflected from the article.

11. The apparatus of claim 10 wherein the consistency-creating means comprises a concave mirror, and wherein the directing means further comprises a lens for focusing the beam on the article.

12. The apparatus of claim 10 further comprising means for converging the parallel scanning range of the beam into an angular range after the beam has either struck a defect or passed through or reflected from the article to allow for the use of smaller stopping means and smaller collecting means without reducing sensitivity.

13. The apparatus of claim 12 wherein the stopping means is located at the focal point of the converging angular range.

14. An apparatus for detecting defects in a transparent article which cause deflection of a laser beam when the laser beam strikes a defect in the transparent article, comprising:

a laser beam;

a lens to focus the laser beam;

a scanner which scans the laser beam focused by the lens across a desired angular range;

a first concave mirror which receives the laser beam from the scanner, converts the angular range of the laser beam to a generally parallel range so that the beam is directed at a portion of the surface of the transparent article at approximately the same angle of incidence, and focuses the generally parallel range of the beam across the transparent article at an angle of incidence with the surface of the transparent article ranging from 70 to 90 degrees;

a second concave mirror which receives the laser beam from the first concave mirror after the beam has passed through the transparent article, and which converts the generally parallel range of the beam to an angular range, unless the laser beam has been sufficiently deflected to avoid striking the second concave mirror;

a plate which stops the laser beam reflected from the second concave mirror when the beam is not deflected or sufficiently deflected by the defect to avoid the plate, but wherein the plate will not stop a beam which has been deflected outside of the perimeter of the plate; and a photodetector which can collect the beam which was reflected from the second concave mirror after striking the defect and being deflected sufficiently off course such that the beam passed through the transparent article and was not stopped by the plate, but not deflected beyond the perimeter of the photodetector.

15. An apparatus for detecting defects in a transparent article which cause the deflection of a scanning beam when the beam is directed through the transparent article comprising:

a scanner for creating a scanning beam;

means for directing the scanning beam at the article at an angle of incidence ranging from 70 to 90 degrees; and means for collecting the beam having a first portion of its surface area which is struck by the scanning beam when the beam is deflected by a defect and passes through the transparent article, and having a second portion within the first portion which is struck when the beam is undeflected by the defect and passes through the transparent article, wherein the first portion has a different degree of sensitivity to the beam than the second portion so that the apparatus can distinguish between a deflected beam and an undeflected beam.

16. An apparatus for detecting defects in a transparent article which cause deflection of a laser beam when the laser beam strikes a defect in the transparent article and passes through the transparent article, comprising:

a laser beam;

a lens to focus the laser beam;

a scanner which scans the laser beam focused by the lens across a desired angular range;

a first concave mirror which receives the laser beam from the scanner, converts the angular range of the laser beam to a parallel range so that the beam is directed at the transparent article at the same angle of incidence, and focuses the parallel range of the beam across the transparent article at an angle of incidence with the surface of the transparent article ranging from 70 to 90 degrees;

a second concave mirror which receives the laser beam from the first concave mirror after the beam has passed through the transparent article, and which converts the parallel range of the beam to an angular range, unless the laser beam has been sufficiently deflected to avoid striking the second mirror;

a first photodetector which collects the beam reflected from the second concave mirror, when the beam had not been deflected or sufficiently deflected by the defect to avoid the first photodetector, but wherein the photodetector will not collect a beam which has been deflected outside of the perimeter of the first photodetector due to the angle of incidence at which the laser beam is directed toward the transparent article; and at least one additional photodetector which can collect the beam which was reflected from the second concave mirror after striking the defect and being deflected sufficiently off course such that the beam was not collected by the first photodetector.

17. A method useful for detecting defects in a transparent article which cause slight deflection of a laser beam when the laser beam strikes a defect in the transparent article, the transparent article having a side edge, the method comprising the steps of:

directing the beam through the transparent article at an angle of incidence ranging from 70 degrees to 90 degrees and such that the beam approaches the transparent article from beyond the side edge;

stopping the beam when the beam passes through the transparent article and is not sufficiently deflected by the transparent article; and collecting the beam when the beam is deflected sufficiently off course by striking the transparent article such that the beam passes through the transparent article and is not stopped by the stopping means, but is not deflected beyond the perimeter of the collecting means.

18. The method of claim 17 further comprising the step of converging the beam after the beam is directed across the article and has either struck a defect or passed through or reflected from the article.

19. The method of claim 17, wherein the large angle of incidence ranges from 75 to 85 degrees.

20. The method of claim 17, wherein the beam is directed across the article in a generally parallel scanning range so that the beam strikes the portion of the article being scanned at approximately the same angle of incidence.

21. The method of claim 17, wherein the transparent article comprises a flexible film, and wherein the flexible film does not rest against a back-up member where the beam scans through the flexible film.

22. An apparatus for detecting defects in an article which cause the deflection of a scanning beam when the beam is directed at the article, wherein the article has a surface and a side edge, and wherein the apparatus comprises:

means for scanning a beam across at least a portion of the surface of the article, wherein the scanning means is positioned other than directly above the article so that the beam approaches the surface of the article from across the side edge of the article; and means for determining whether the beam is deflected by a defect in the article.

23. The apparatus of claim 22, wherein the article has a length and a width and is moveable in a longitudinal direction, and wherein the beam can be scanned toward the article in a transverse direction.

24. An apparatus for detecting defects in at least a portion of an article which cause the deflection of a scanning beam when the beam is directed at the article comprising:

means for scanning the beam at the article, wherein the scanning means comprises an optical element having a width which is less than the width of the portion of the article across which the beam is scanned; and means for determining whether the beam has been deflected by a defect in the article.

25. The apparatus of claim 24, wherein the article has a surface, and wherein the optical element can scan the beam across the entire width of the surface of the article.

26. The apparatus of claim 25, wherein the optical element can scan the beam in a generally parallel scanning range.

27. An apparatus for detecting defects in at least a portion of an article which cause the deflection of a scanning beam when the beam is directed at the article comprising:

means for scanning the beam in a generally parallel scanning range, wherein the scanning range has a width which is less than the width of the portion of the article being scanned by the beam; and means for determining whether the beam has been deflected by a defect in the article.

28. The apparatus of claim 27, wherein the scanning means comprises a mirror which scans the beam across at least a portion of the article generally orthogonally to the side edges of the article.

29. The apparatus of claim 27, wherein the determining means comprises a sensor which is positioned so that the beam will strike the sensor when the beam is not deflected by a defect.

30. The apparatus of claim 27, wherein the determining means comprises a sensor which is positioned so that the beam will strike the sensor when the beam is deflected by a defect.

31. A method of detecting defects or variations in or on an article which cause deflection of a beam when the beam strikes a defect in the article, comprising the steps of:

scanning a beam across at least a portion of the surface of the article, wherein the beam is scanned from a position other than from directly above the article so that the beam approaches the surface of the article from across the side edge of the article; and determining whether the beam is deflected by the defect in the article.

32. A method of detecting defects or variations in or on an article which cause deflection of a beam when the beam strikes a defect in the article, comprising the steps of:

scanning the beam at the article with an optical element which has a width which is less than the width of the portion of the article across which the beam is scanned; and determining whether the beam has been deflected by a defect in the article.

33. The method of claim 32, wherein the beam is scanned across a scanning width which is less than the width of the portion of the article scanned by the scanning beam.

34. A method for detecting defects in an article which cause the deflection of a beam when the beam is scanned at the article, the article having a side edge, the method comprising the steps of:

scanning a beam through the article at an angle of incidence ranging from 70 to 90 degrees and such that the beam approaches the article from beyond the side edge;

collecting the beam with a first portion of a collector when the beam is deflected by a defect;

collecting the beam with a second portion of the collector when the beam is undeflected by the defect, wherein the second portion has a different degree of sensitivity to the beam than the first portion; and distinguishing between a deflected beam and an undeflected beam based on the different degrees of sensitivity.

35. An apparatus useful for detecting defects in a moving web, the moving web having a first side edge, a second side edge, and a web surface, the apparatus comprising:

means for directing a scanning beam at the web surface at an angle of incidence ranging from 70 degrees to 90 degrees and such that the scanning beam approaches the web surface from beyond one of the first and second side edges, the moving web being transparent to the scanning beam such that the scanning beam can pass through the moving web; and means for stopping the beam when the beam passes through the moving web and is not sufficiently deflected by the defect in the moving web; and means for collecting the scanning beam when the beam is deflected sufficiently off course by striking the defect as the beam passes through the moving web such that the beam is not stopped by the stopping means but not deflected beyond the collecting means.

36. An apparatus useful for detecting defects in a moving web, the moving web having a side edge and a web surface, the apparatus comprising:

means for directing a scanning beam through the web surface at an angle of incidence ranging from 70 degrees to 90 degrees and such that the scanning beam approaches the web surface from beyond the side edge, the moving web being transparent to the scanning beam; and means for collecting the scanning beam when the scanning beam passes through the web.

37. The apparatus of claim 36, the directing means being configured such that the scanning beam approaches the web surface generally perpendicular to the side edge.

38. The apparatus of claim 36, the directing means comprising means for directing the scanning beam in a generally parallel scanning range when approaching the moving web.

39. The apparatus of claim 36, the directing means being configured such that the angle incidence is substantially the same as the scanning beam scans across the web.

40. The apparatus of claim 36, the web moving in a downweb direction, the directing means directing the scanning beam at the web in a cross-web direction, the cross-web direction being generally perpendicular to the downward direction.

41. The apparatus of claim 36, the directing means being means for directing a scanning beam through the web at an angle of incidence ranging from 75 degrees to 85 degrees.

42. The apparatus of claim 36, the directing means being means for directing a scanning beam through the web at an angle of incidence of approximately 80 degrees.

43. A method useful for detecting defects in a moving web, the web having a side edge and a web surface, the method comprising the steps of:

directing a scanning beam through the web surface at an angle of incidence ranging from 70 degrees to 90 degrees and such that the scanning beam approaches the web surface from beyond the side edge, the moving web being transparent to the scanning beam; and collecting the scanning beam when the scanning beam passes through the web.

44. A method for enhancing the detectability of a defect in a transparent fluid after the transparent fluid is coated onto a first side of a transparent article, the transparent article having a side edge, the method comprising the step of scanning a beam through the transparent fluid and the transparent article at an angle of incidence to produce a deflection of the beam when the beam strikes the defect and passes through the transparent fluid and transparent article, the angle of incidence ranging from 70 to 90 degrees, and the beam being scanned toward the transparent article from beyond the side edge.

45. The method of claim 44, the angle of incidence ranging from 75 to 85 degrees.

46. The method of claim 44, the angle of incidence being substantially constant when the beam is scanned across the transparent fluid.

47. A method for enhancing the detectability of a defect in a transparent fluid after the transparent fluid is coated onto a first side of a transparent article, the transparent fluid having a fluid first side edge, the method comprising the step of scanning a beam through the transparent fluid and the transparent article at an angle of incidence to produce a deflection of the beam when the beam strikes the defect and passes through the transparent fluid and transparent article, the angle of incidence ranging from 70 to 90 degrees, and the beam being scanned toward the transparent fluid from beyond the fluid first side edge.

48. The method of claim 47, the angle of incidence ranging from 75 to 85 degrees.

49. The method of claim 47, the angle incidence being substantially constant when the beam is scanned across the transparent fluid.

50. The method of claim 47, the transparent article being a transparent polymeric film having a film first side edge adjacent to the fluid first side edge, the transparent fluid having been coated such that the fluid first side edge extends to coincide with the film first side edge.

51. The method of claim 47, the transparent article being a transparent polymeric film having a film first side edge adjacent to the fluid first side edge, the transparent fluid having been coated such that the fluid first side edge does not extend to coincide with the film first side edge.

52. A method for coating a transparent fluid onto a transparent article and for enhancing the detectability of a defect in a transparent fluid after the transparent fluid is coated onto a first side of a transparent article, the transparent fluid having a fluid first side edge, the method comprising the step of scanning a beam through the transparent fluid and the transparent article at an angle of incidence to produce a deflection of the beam when the beam strikes the defect and passes through the transparent fluid and transparent article, the angle of incidence ranging from 70 to 90 degrees, and the beam being scanned toward the transparent fluid from beyond the fluid first side edge.

53. The method of claim 52, the angle of incidence ranging from 75 to 85 degrees, the angle of incidence being substantially constant when the beam is scanned across the transparent fluid, the transparent article having a film first side edge adjacent to the fluid first side edge, the transparent fluid having been coated such that the fluid first side edge does not extend to coincide with the film first side edge.

* * * * *